United States Patent [19]
Mariani

[11] Patent Number: 5,954,557
[45] Date of Patent: Sep. 21, 1999

[54] LIFE VEST WITH AN INTERNALLY LOCATED BACK SUPPORT

[76] Inventor: Richard D. Mariani, 109 S. Orchard Dr., Burbank, Calif. 91506

[21] Appl. No.: 08/998,745

[22] Filed: Dec. 29, 1997

[51] Int. Cl.$^6$ ........................................................ B63C 9/08
[52] U.S. Cl. .............................................. 441/106; 441/108
[58] Field of Search ........................ 441/80, 88, 106–108, 441/111–118; 2/44

[56] References Cited

U.S. PATENT DOCUMENTS

| | | | |
|---|---|---|---|
| 4,820,221 | 4/1989 | Aubrey | 441/106 |
| 4,936,805 | 6/1990 | Piatt, Jr. | 441/106 |
| 5,328,398 | 7/1994 | Aubrey | 441/106 |
| 5,402,539 | 4/1995 | Hewitt | 2/44 |
| 5,450,627 | 9/1995 | Grilliot et al. | 2/44 |
| 5,611,084 | 3/1997 | Garry et al. | 2/44 |

*Primary Examiner*—Ed L. Swinehart

[57] ABSTRACT

The life vest of the present invention is specifically adapted to protect a user's back. This protection is achieved by way of a rigid back support which is interconnected to the internal surface of the life vest. This interconnection is achieved by way of a series of straps secured upon the internal surface of the vest. The straps, in turn, are connected to the life jacket by way of stitching or such. Through this interconnection, the life jacket is allowed a certain degree of freedom. More specifically, the life jacket is permitted vertical movement relative to the back brace.

5 Claims, 3 Drawing Sheets

LIFE VEST WITH AN INTERNALLY LOCATED BACK SUPPORT

BACKGROUND OF THE INVENTION

1. Field of the Invention

The present invention relates to a life vest and more particularly pertains to a life vest with an internally located back support.

2. Description of the Prior Art

The use of life vests is known in the prior art. More specifically, life vests are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,936,805 to Piatt, Jr. discloses a life vest with a back brace. U.S. Pat. No. 4,551,107 to Scheurer discloses a floatation garment. U.S. Pat. No. Design 361,115 to Lucius discloses a life vest for water skiers. U.S. Pat. No. 4,820,221 to Aubrey discloses an upper body buoyant garment with an implanted positive lumbar support structure. U.S. Pat. No. 4,665,908 to Calkin discloses a extrication and spinal restraint device. Lastly, U.S. Pat. No. 4,137,585 to Wright discloses a buoyancy compensator and inflation system.

In this respect, the life vest of the present invention substantially departs from the conventional concepts and designs of the prior art, and in so doing provides an apparatus primarily developed for the purpose of providing back support for a user of the life vest.

Therefore, it can be appreciated that there exists a continuing need for improvements in life vests. In this regard, the present invention substantially fulfills this need.

SUMMARY OF THE INVENTION

In view of the foregoing disadvantages inherent in the known types of life vests now present in the prior art, the present invention provides a vertically adjustable back support positioned within a life vest. As such, the general purpose of the present invention, which will be described subsequently in greater detail, is to provide back support to a wearer of a life vest.

To attain this, a life vest adapted to be worn by a user, the vest having an internally located back support, the life vest comprising a vest having a lower extent adapted to be secured proximate a user's waist, an upper extent with a neck opening formed therein, a front surface having a vertical opening formed therein, an upper portion of the vertical opening integral with a lower portion of the neck opening, a first arm hole formed within a first side of the vest, a second arm hole formed within a second side of the vest, at least one horizontally oriented strap positioned upon an internal surface of the vest, the strap having first and second ends secured to the internal surface of the vest and a free intermediate extent therebetween; a back support having, a first end, a second end and an intermediate extent therebetween, two vertical straps coupled at their ends to the back support, the horizontal strap of the vest being threaded through the straps of the support, the back support thus being interconnected to the lower extent of the vest, the interconnection functioning to allow the vest a small degree of vertical freedom.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved life vest adapted to be worn by a user. The vest includes a life vest adapted to be worn by a user, the vest having an internally located back support, the lift vest comprising in combination; a vest having a lower extent adapted to be secured proximate a user's waist, an upper extent with a neck opening formed therein, a front surface having a vertical opening formed therein, an upper portion of the vertical opening integral with a lower portion of the neck opening, closure means for use in selectively closing the vertical opening, a first arm hole formed within a first side of the vest, a second arm hole formed within a second side of the vest, at least one horizontal strap positioned upon an internal surface of the back of the vest at the lower extent, the strap having first and second ends secured to the internal surface of the vest and a free intermediate extent therebetween, the vest being formed of a water resistant and buoyant material; a back support having a thickness, a first end, a second end and an intermediate extent therebetween, securing means including a pile type fastener in facing relationships at the ends of the back support with straps having buckles at their free ends for selectively securing the first and second ends together, a plurality of elongated reinforcing members positioned within pockets formed in the thickness of the intermediate extent for use in supporting the back of a user, two vertical straps with intermediate openings secured to the intermediate extent of the back support, each of the vertical straps of the back support being threaded through the horizontal strap, the back support thus being interconnected to the lower extent of the vest, the interconnection functioning to allow the vest a small degree of vertical freedom.

It is another object of the present invention to provide a life vest with a fixed positional back support.

It is a further object of the present invention to provide a life vest which allows a small degree of movability separate from the back brace upon impact with the water.

An even further object of the present invention is to provide such a life vest and back support which is susceptible of a low cost of manufacture with regard to both materials and labor, and which accordingly is then susceptible of low prices of sale to the consuming public, thereby making such life vests economically available to the buying public.

Still yet another object of the present invention is to provide a life vest and back support which provide in the apparatuses and methods of the prior art some of the advantages thereof, while simultaneously overcoming some of the disadvantages normally associated therewith.

Still another object of the present invention is to provide a life vest system wherein a life vest and back support are independently secured about a user to enable greater security.

Lastly, it is an object of the present invention to provide a life vest with a back support internally secured in a manner which allows a small amount of vertical freedom therebetween.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Similar reference characters refer to similar parts throughout the several views of the drawings.

DESCRIPTION OF THE PREFERRED EMBODIMENT

Figure 1:
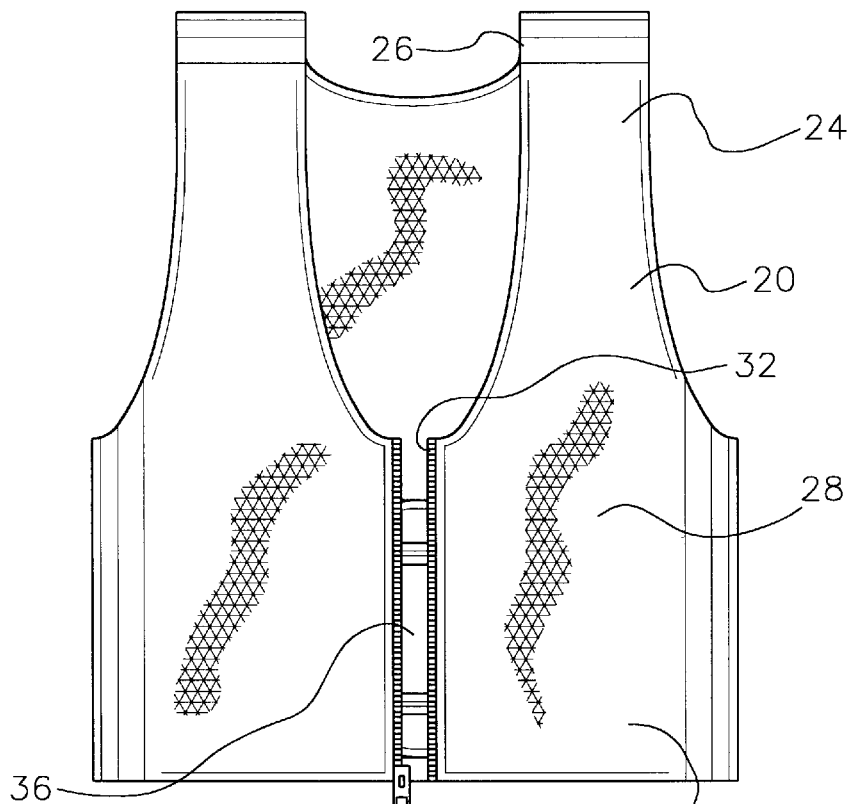
FIG. 1 is a front view of the life vest of the present invention.

With reference now to the drawings, and in particular to FIG. 1 thereof, the life vest of the present invention is depicted. The life vest of the present invention is specifically configured for use with a back support adapted to protect a user's back. This protection is achieved by way of a rigid back support which is interconnected to the internal surface of the life vest. This interconnection is achieved by way of a single horizontal strap secured upon the internal surface of the vest. The horizontal strap, in turn, is connected to the back support by way of a series of aligned vertical straps secured to the back support. Through this interconnection, the life vest is allowed a certain degree of freedom with respect to the back brace. More specifically, the life vest is permitted vertical movement relative to the back support when the vest is worn by a user. The various components of the present invention, and the manner in which they interrelate, will be described in greater detail hereinafter.

Figure 2:
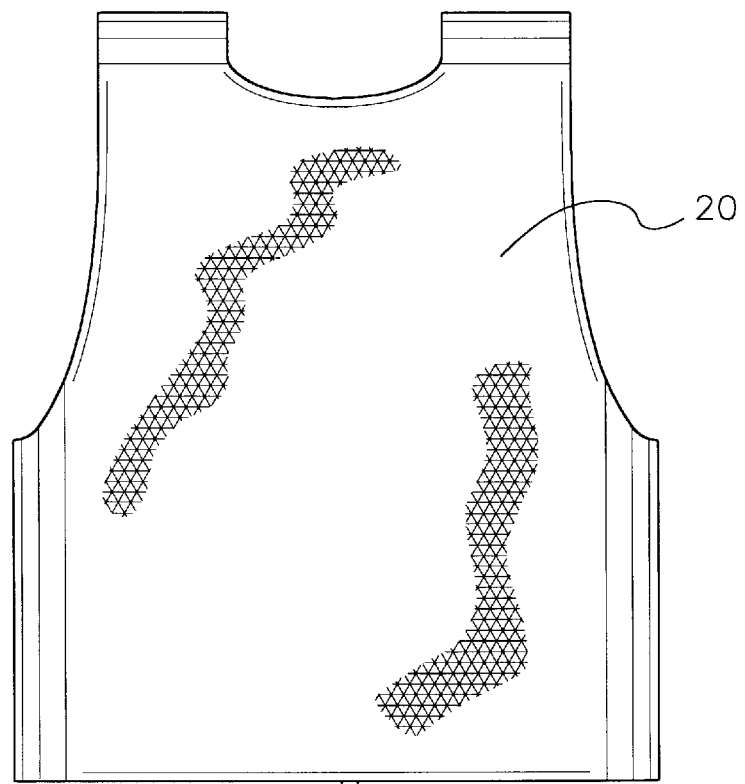
FIG. 2 is a back view of the life vest of the present invention.

The vest 20 of the present invention is defined by a lower extent 22, which adapted to be secured proximate a user's waist, and an upper extent 24. A neck opening 26 is formed within the upper extent 24 of the vest. Additionally, the vest 20 includes a front surface 28 with a vertical opening 32 formed therein. As illustrated in FIG. 1, an upper portion of the vertical opening 32 is integral with a lower portion of the neck opening 26. Furthermore, closure means are included for use in selectively closing the vertical opening 32. As illustrated in FIG. 1 this closure means can take the form of a zipper. With reference again to FIGS. 1 and 2, a first arm hole is formed within a first side of the vest, and likewise a second arm hole is formed within a second side of the vest.

Figure 4:
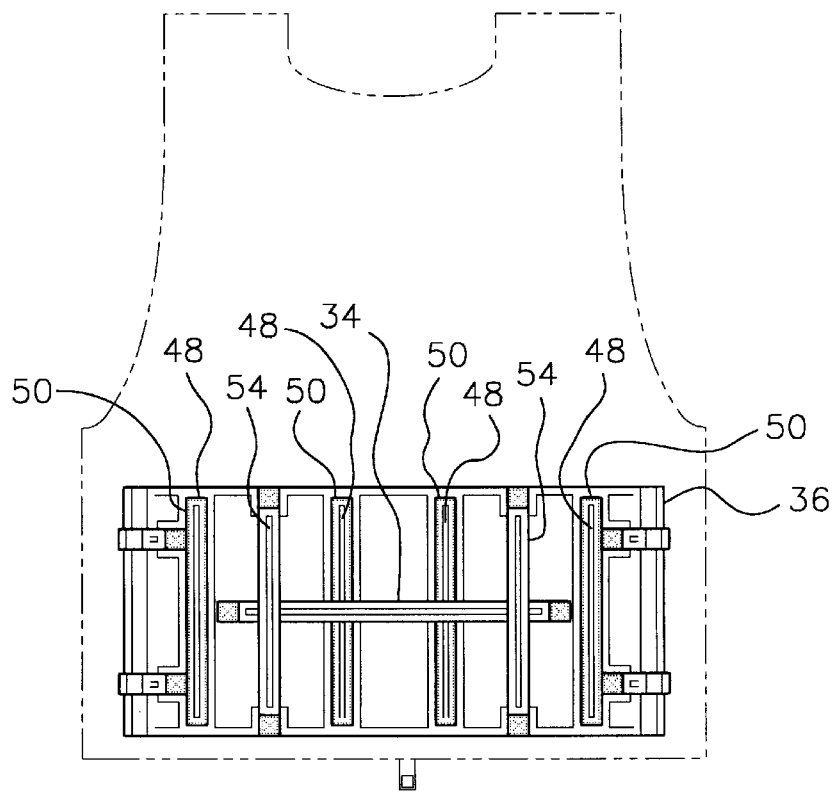
FIG. 4 is a rear view of the back support with the life vest illustrated in phantom lines.

With reference to FIG. 4, at least one horizontally oriented strap 34 is positioned upon an internal surface of the vest at the lower extent 22. The horizontal strap is defined by first and second ends secured as by stitching to the internal surface of the vest. Additionally, the strap 34 has a free intermediate extent therebetween. The function of the strap 34 will be described in greater detail hereinafter. Lastly, the vest 20 of the present invention is preferably formed of a water resistant and buoyant material.

Figure 3:
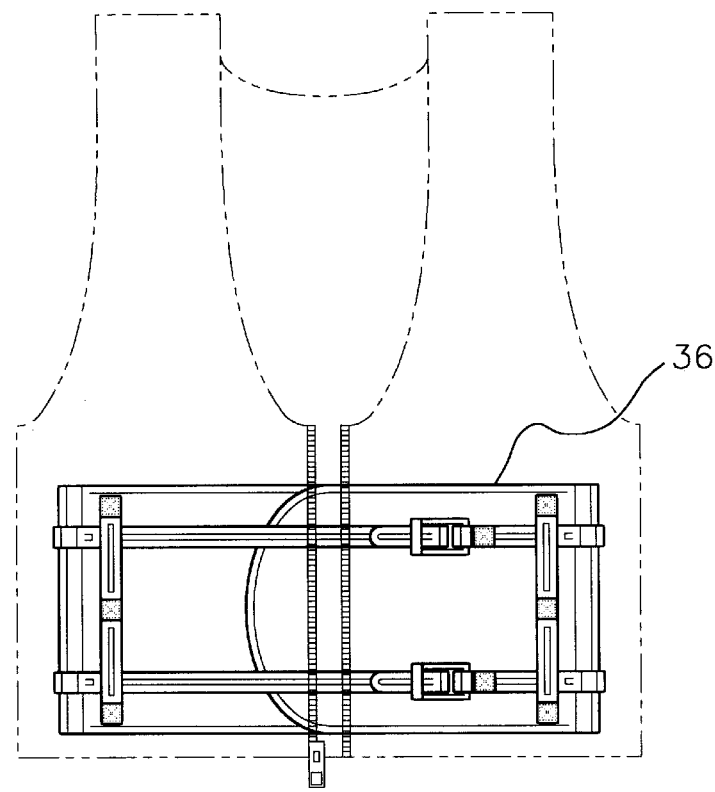
FIG. 3 is a front view of the back support with the life vest illustrated in phantom lines.
Figure 5:
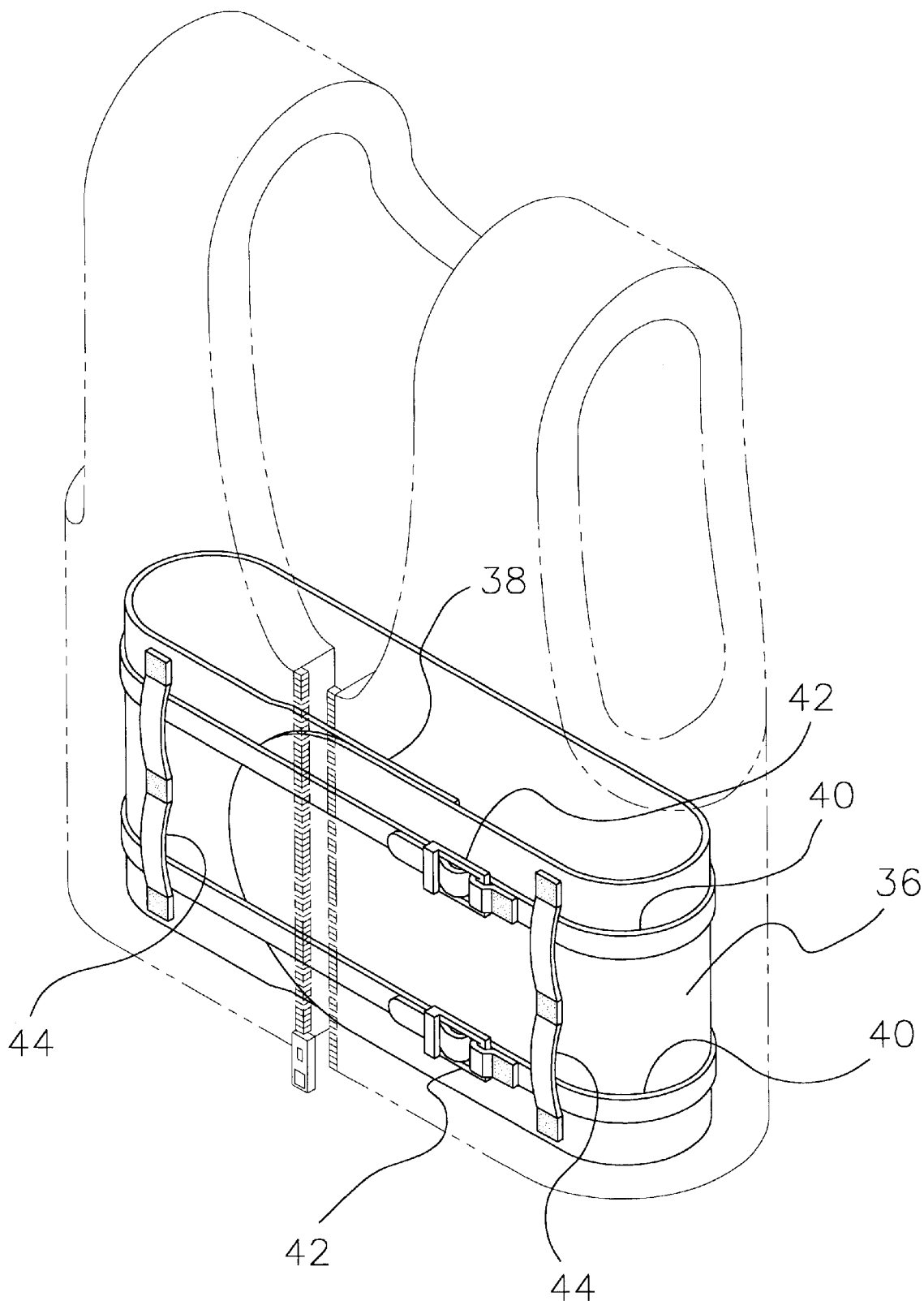
FIG. 5 is a perspective view of the back support and life vest in phantom lines.

The back support 36 component of the present invention is depicted in both FIGS. 3, 4 and 5. This back support 36 is defined by a thickness, a first end, a second end and an intermediate extent therebetween. Additionally, securing means are included for selectively securing the first and second ends of the back support together. Such securement means includes a pile type fastener 38 on facing surfaces at the adjacent ends of the vest. Such securement means also includes straps 40 having ends stitched to the back of the back support plus buckles 42 at the free ends with loop straps 44 to hold the straps 40 at a proper height orientation. Thus, the vest and the back support can be secured independently of one another.

In the preferred embodiment, a plurality of elongated rigid reinforcing members 48 are positioned within pockets 50 forming the thickness of the intermediate extent of the back support 36. Such reinforcing members 48, preferably, four vertically disposed essentially rigid rods of plastic or metal, are for use in supporting the back of a user. The back support 36 itself would consist of or be made out of a wetsuit type material (NEOPRENE) or a cotton/nylon type blend combination.

The back support 36 also includes two vertical straps 54 coupled at their ends as by stitching to an intermediate extent of the back support 36. Each of the straps of the back brace 36 is threaded through the horizonal strap 34 of the vest. In this manner the back support may be interconnected to the lower extent 22 of the vest 20. The interconnect functions to allow the vest a small degree of vertical freedom separate from the back brace.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A life vest adapted to be worn by a user, the vest having an internally located back support, the lift vest comprising in combination:

a vest having a lower extent adapted to be secured proximate a user's waist, an upper extent with a neck opening formed therein, a front surface having a vertical opening formed therein, an upper portion of the vertical opening integral with a lower portion of the neck opening, closure means for use in selectively closing the vertical opening, a first arm hole formed within a first side of the vest, a second arm hole formed within a second side of the vest, at least one horizontal strap positioned upon an internal surface of the back of the vest at the lower extent, the strap having first and second ends secured to the internal surface of the vest and a free intermediate extent therebetween, the vest being formed of a water resistant and buoyant material;

a back support having a thickness, a first end, a second end and an intermediate extent therebetween, securing means including a pile fastener in facing relationships at the ends of the back support with straps having buckles at their free ends for selectively securing the first and second ends together, a plurality of elongated reinforcing members positioned within pockets formed in the thickness of the intermediate extent for use in supporting the back of a user, two vertical straps with intermediate openings secured to the intermediate extent of the back support, each of the vertical straps of the back support being threaded through the horizontal strap, the back support thus being interconnected to the lower extent of the vest, the interconnection functioning to allow the vest a small degree of vertical freedom.

2. A life vest adapted to be worn by a user, the vest having an internally located back support, the lift vest comprising:

a vest having a lower extent adapted to be secured proximate a user's waist, an upper extent with a neck opening formed therein, a front surface having a vertical opening formed therein, an upper portion of the vertical opening integral with a lower portion of the neck opening, a first arm hole formed within a first side of the vest, a second arm hole formed within a second side of the vest, at least one horizontally oriented strap positioned upon an internal surface of the vest, the strap having first and second ends secured to the internal surface of the vest and a free intermediate extent therebetween;

a back support having, a first end, a second end and an intermediate extent therebetween, two vertical straps coupled at their ends to the back support, the strap of the vest being threaded through the straps of the support, the back support thus being interconnected to the lower extent of the vest, the interconnection functioning to allow the vest a small degree of vertical freedom.

3. The life vest as described in claim 2 further comprising:

closure means for use in selectively closing the vertical opening of the vest.

4. The life vest as described in claim 2 wherein:

the vest is formed of a water resistant and buoyant material.

5. The life vest as described in claim 2 further comprising:

a plurality of elongated reinforcing members positioned within pockets formed in the thickness of the intermediate extent of the back support for use in supporting the back of a user.

* * * * *